United States Patent
Greenhalgh

(10) Patent No.: US 6,346,117 B1
(45) Date of Patent: Feb. 12, 2002

(54) BAG FOR USE IN THE INTRAVASCULAR TREATMENT OF SACCULAR ANEURYSMS

(75) Inventor: E. Skott Greenhalgh, Wyndmoor, PA (US)

(73) Assignee: Prodesco, Inc., Perkasie, PA (US)

( * ) Notice: Subject to any disclaimer, the term of this patent is extended or adjusted under 35 U.S.C. 154(b) by 0 days.

(21) Appl. No.: 09/517,273

(22) Filed: Mar. 2, 2000

(51) Int. Cl.$^7$ .............................................. A61M 29/00
(52) U.S. Cl. ...................................................... 606/200
(58) Field of Search ................................. 606/151, 113, 606/114, 127, 213, 157, 200, 108, 1

(56) References Cited

U.S. PATENT DOCUMENTS

| | | | |
|---|---|---|---|
| 5,122,136 A | 6/1992 | Guglielmi et al. ............. 606/32 |
| 5,330,483 A | * 7/1994 | Heaven et al. ............... 606/127 |
| 5,334,210 A | * 8/1994 | Gianturco .................... 606/151 |
| 5,397,331 A | 3/1995 | Himpens et al. ............ 606/151 |
| 5,496,277 A | 3/1996 | Termin et al. ............... 604/104 |
| 5,713,848 A | 2/1998 | Dubrul et al. ................ 604/22 |
| 5,718,159 A | 2/1998 | Thompson ..................... 87/33 |
| 5,814,064 A | 9/1998 | Daniel et al. ............... 606/200 |
| 5,925,060 A | 7/1999 | Forber ......................... 606/191 |
| 5,941,896 A | 8/1999 | Kerr ............................. 606/200 |
| 5,954,745 A | 9/1999 | Gertler et al. ............... 606/200 |
| 6,010,498 A | 1/2000 | Guglielmi .................... 606/32 |
| 6,022,336 A | 2/2000 | Zadno-Azizi et al. ......... 604/96 |
| 6,024,754 A | 2/2000 | Engelson .................... 606/213 |
| 6,027,520 A | 2/2000 | Tsugita et al. .............. 606/200 |
| 6,059,814 A | 5/2000 | Ladd ........................... 606/200 |
| 6,066,149 A | 5/2000 | Samson et al. ............. 606/159 |
| 6,142,987 A | 11/2000 | Tsugita ........................ 604/500 |

* cited by examiner

*Primary Examiner*—Kevin Truong
(74) *Attorney, Agent, or Firm*—Synnestvedt & Lechner LLP

(57) ABSTRACT

A bag for use in the intravascular treatment of saccular aneurysms and a method of forming the bag are disclosed. The bag is formed from a plurality of flexible, resilient filamentary members braided into a tubular sleeve and biased into a first shape having an expanded first diameter sized to substantially fill the aneurysm. The bag is resiliently deformable into a second shape having a diameter smaller than the first and sized to slidingly interfit within the lumen of a catheter. An opening is provided in the bag to receive a clotting medium, such as a platinum wire, on which blood clots can be induced to form by mechanical or electrolytic means. A closure is provided by biasing the filamentary members to form a constriction around the opening. In use the, bag is inserted into a saccular aneurysm via the catheter and expands to its first diameter upon release therefrom. Interstices between the interbraided filamentary members provide pores allowing blood from the aneurysm to enter the bag when the bag is positioned within the aneurysm. The clotting medium wire is packed into the bag, blood clots on the wire and occludes the aneurysm, sealing it off from the blood stream and preventing rupture. The wire is released from the catheter and is contained within the bag in the aneurysm.

26 Claims, 7 Drawing Sheets

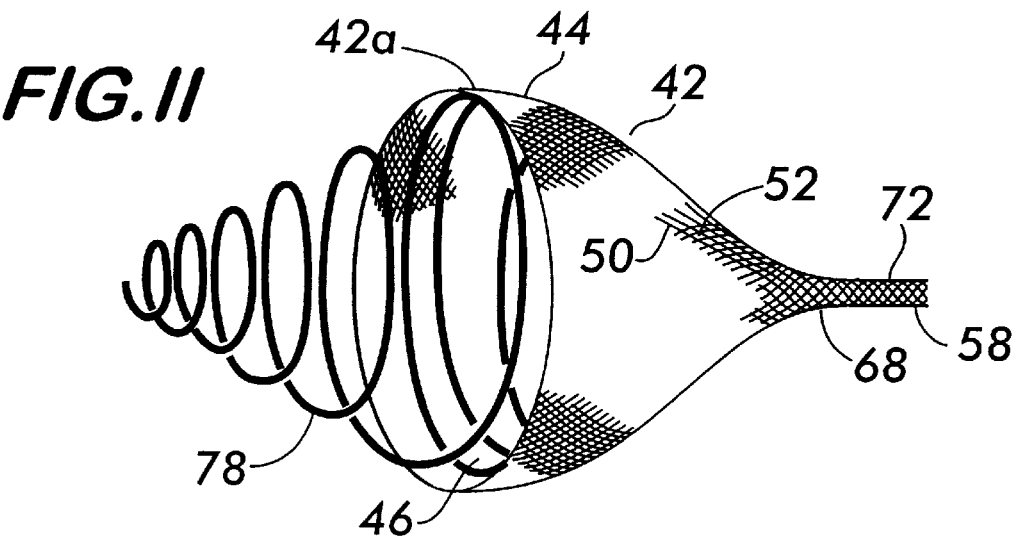

FIG.11

```
┌─────────────────────────────────┐
│    BRAID YARNS TO FORM BAG      │
│    (USE MANDREL IF NECESSARY)   │
└─────────────────────────────────┘
                │
                ▼
┌─────────────────────────────────┐
│   INTERBRAID SUPPLEMENTAL       │
│ FILAMENTARY MEMBERS WITH YARNS  │
│         FOR BIASING OR          │
│    AUGMENTATION OF BIASING      │
└─────────────────────────────────┘
                │
                ▼
┌─────────────────────────────────┐
│  BIAS YARNS INTO FIRST SHAPE STATE │
└─────────────────────────────────┘
                │
                ▼
┌─────────────────────────────────┐
│  COLLAPSE BAG TO SECOND SHAPE STATE │
│   AND POSITION IN CATHETER LUMEN    │
└─────────────────────────────────┘
```

FIG.12

BAG FOR USE IN THE INTRAVASCULAR TREATMENT OF SACCULAR ANEURYSMS

FIELD OF THE INVENTION

This invention relates to an intravascular device used in the treatment of aneurysms, and especially in the occlusion of cerebrovascular saccular aneurysms.

BACKGROUND OF THE INVENTION

Saccular aneurysms occur at the branching of arteries in the body and comprise a sack-like formation of the artery wall which extends outwardly from the bifurcation point between the arterial branches. The aneurysm has a neck forming the juncture with the artery and is capped by a dome. During formation of the aneurysm, the arterial internal elastic lamina disappears at the base of the neck, the sack wall thins and weakens and connective tissue replaces smooth-muscle cells. The aneurysm tends to rupture at the dome and bleeding ensues.

Rupture of a cerebrovascular saccular aneurysm is especially serious due to the associated high mortality rate (10% within the first day of rupture, 25% within three months) and the major neurological deficits experienced by those who survive the initial hemorrhage. Naturally, therapeutic treatment of cerebrovascular aneurysms emphasizes preventing the initial rupture.

Intravascular Catheter Treatment Technique

Intravascular catheter techniques for treating saccular aneurysms are discussed in U.S. Pat. No. 5,122,136, hereby incorporated by reference, and U.S. Pat. No. 6,010,498, also hereby incorporated by reference.

The techniques described in these patents can be summarized with reference to FIGS. 1 and 2, which show a saccular aneurysm 20 formed in an artery 22 at a bifurcation point 24. The treatment techniques involve positioning a catheter 26 at the artery bifurcation point 24, the catheter tip 28 extending partially into the neck 30 of the aneurysm 20. Once the catheter is in position, a length of platinum or platinum alloy wire 32 is snaked through the catheter's lumen 34 through the aneurysm neck 30 and into the aneurysm 20. The wire 32 has a length between 0.4 and 20 inches (1 and 50 cm), is relatively thin (between 0.001–0.005 inches in diameter) and flexible and loops and tangles randomly as it is packed into the aneurysm. Blood which would normally circulate under pressure into the aneurysm, causing it to enlarge, weaken and rupture, begins to form clots 36 on the platinum wire tangle and eventually the clots merge and enlarge to form an occlusion 38 (see FIG. 2) which seals off the aneurysm from the blood flow, preventing further enlargement and rupture.

Clotting on the wire 32 within aneurysm 20 is promoted by mechanical and/or electrical means. Forming the wire 32 into a continuous coil having a diameter between 0.010 and 0.020 inches will promote clotting mechanically by providing a multiplicity of adjacent cites on the wire where clots can adhere and join together. Running an electrical current of approximately 0.01 to 2 milliamperes through the wire with the wire forming the anode of the circuit at a positive 0.1 to 6 volts will cause clots to form by the phenomenon of electrothrombosis. Electrothrombosis takes advantage of the fact that white blood cells, red blood cells, platelets and fibrogen are typically negatively charged in blood having normal pH, and these negatively charged components are, therefore, electrostatically attracted to the positively charged wire. The electrostatic attraction of the blood components promotes and speeds the clotting process.

Once the appropriate length of wire is positioned in the aneurysm and the occlusion has been formed, the wire 32 is released at or near the neck 30 of the aneurysm and the catheter is withdrawn (FIG. 2). Wire release is effected by any one of several means, for example, mechanical means or electrolytic means.

Release of the wire by mechanical means involves another wire (not shown) which is attached in tandem with the platinum wire 32. The other wire extends through the catheter and provides the means to push the platinum wire through the catheter and into the aneurysm. The other wire has a spring biased mechanical clasp (not shown) at its end which grips an end 40 of wire 32 (see FIG. 2). The clasp remains engaged with the wire end 40 as long as the clasp remains within the catheter lumen. To release wire 32, the clasp is temporarily extended from the lumen, the spring biasing opens the clasp and the wire end 40 is released. The other wire and the clasp are drawn back into the catheter lumen, which is then removed from the artery.

For release of the wire by electrolytic means, the end 40 of platinum wire 32 is attached to the other wire by a wire segment formed of stainless steel (not shown). When it is desired to release the platinum wire, the stainless steel segment is positioned outside of the catheter lumen and exposed to the blood stream. Application of an electrical current through the exposed stainless steel portion causes it to corrode away, releasing the platinum wire 32.

While this catheter technique holds great promise of effective treatment for preventing aneurysm rupture, especially cerebrovascular saccular aneurysms, it has a significant drawback in that it is not always possible to ensure that the entire length of wire 32 remains within the aneurysm. Even if the entire length of wire is successfully positioned wholly within the aneurysm during the procedure, it has been found that the end 40 of the wire can work its way out of the aneurysm over time, extend through the aneurysm neck 30 and protrude into the artery 22 as illustrated in FIG. 2. Blood flowing through the artery past the wire end will form a clot 36 on the protruding wire end 40, and this clot could separate from the wire end and cause a stroke or embolism. Statistical results predict that as many as 5% of the patients treated by this technique will suffer complications caused by the wire extending through the aneurysm neck and into the artery. Clearly, there is a need for improving this catheter treatment technique to eliminate the potential for embolisms or stroke as a result of the procedure.

SUMMARY AND OBJECTS OF THE INVENTION

The invention comprises a flexible bag adapted to pass through a catheter lumen and expand upon release from the lumen to substantially occupy a fluid-filled cavity larger than the lumen. The bag is adapted to receive fluid within the cavity. The bag also receives a clotting medium which promotes coagulation of the fluid when in contact with it.

The bag comprises a plurality of interlaced flexible filamentary members and a multiplicity of pores formed by interstices between the interlaced filamentary members. The pores are sized to allow the fluid in the cavity to enter the bag but prevent outward protrusion of the clotting medium out of the bag.

The filamentary members are resiliently biased to assume an expanded first diameter substantially filling the cavity upon release from the catheter lumen. The filamentary members are resiliently deformable to a second diameter smaller than the first diameter, the second diameter being sized to slidingly interfit within the catheter lumen.

Preferably, the bag is used in the intravascular treatment of saccular aneurysms, thus, the aforementioned cavity is the saccular aneurysm, the fluid is blood and the clotting medium comprises a length of wire. The wire length could be contained in the bag while positioned in the catheter or fed into the bag after it is positioned in its expanded diameter within the aneurysm. Preferably, the wire is compatible with human tissue and conducts electricity, thus, allowing a current to be passed to promote clotting by electrothrombosis. Platinum is the preferred wire material because it fulfills the necessary requirements.

Preferably, the wire is fed into the bag through an opening in the bag for receiving the wire. The filamentary members forming the bag are resiliently biased adjacent to the opening to form a constriction in the bag which closes off the opening and prevents the wire from extending outwardly therethrough. The filamentary members are resiliently deformable away from the opening to expand the constriction and allow access to said bag through the opening to feed the wire.

The filamentary members are preferably interlaced by braiding, as it is well known that braided structures exhibit a "trellis effect", wherein the braided members rotate and slide relatively to one another when a force is applied. For the braided bag according to the invention, this effect results in radial contraction of the bag with axial expansion and radial expansion upon axial contraction, thus, allowing the bag to be resiliently deformed from the first expanded diameter into the second, smaller diameter by the application of appropriate tensile force to the bag, as described below.

Multifilament polymer yarns, preferably of polyester, are used for the filamentary members. Other feasible materials include, for example, ePTFE, PTFE, PET, nylon, polyethylene, PGA and PLA. The yarn material is chosen for its compatibility with human tissue, as well as mechanical properties such as elongation, strength, flexibility, toughness and resilience. Monofilament yarns are also used, the yarns having a denier between about 5 and 100.

Although numerous geometries could be used to form the bag, it is preferably braided into the form of an elongated tube or sleeve, the opening being formed at an end of the tube. The tubular form provides several advantages, for example, it allows the bag to be produced on a circular braiding machine, the braid angle is uniform and easily controlled, and the diameter and length of the tube can be varied over a wide range of values. The filamentary members at the open end are biased radially inwardly to form the constriction closing off the opening and preventing the wire clotting medium from extending outwardly through the opening once it is positioned within the bag.

It is sometimes desired to augment the support of the bag and assist it in expanding into the larger diameter upon release from the catheter lumen. Support augmentation is preferably provided by including a plurality of supplemental filaments contiguous with the filamentary members. The supplemental filaments are resiliently biased to conform to a tubular shape having a diameter substantially equal to the first diameter. The supplemental filaments push radially outwardly due to the resilient biasing to augment the support of the bag when it is expanded to the first diameter, but the supplemental filaments are also resiliently deformable into a collapsed shape sized to slidingly interfit within the catheter lumen. Biasing forces within the filaments expand the filaments and the bag to the tubular shape upon release of the bag from the catheter.

Preferably, the supplemental filaments are interbraided with the filamentary members, although they could also be positioned interiorly or exteriorly of the bag. Supplemental members positioned on the bag interior will naturally push outwardly against the interlaced filamentary members to expand the bag, whereas supplemental members on the exterior of the bag must be attached to the bag, for example, as with sutures.

It is advantageous to make the supplemental filaments from radiopaque monofilament wires. This allows the bag to be viewed by means of fluoroscopy or X-ray techniques when it is positioned within the body. Nitinol, a shape-memory metal, is the preferred material because it is biocompatible and has outstanding elastic properties such as a relatively high yield stress providing excellent resilience and flexibility.

Support augmentation is also provided by positioning a continuous flexible stent within the bag. Stents are often used in the repair of vascular aneurysms and provide a supporting structure resiliently biased to conform to a tubular shape. When used with the bag according to the invention, the stent is resiliently biased to form a diameter substantially equal to the first diameter of the bag. The stent supports the bag by pushing radially outwardly when expanded to the first diameter. The stent is also resiliently deformable into a collapsed shape sized to slidingly interfit within the catheter lumen. Biasing forces within the stent expand it to the tubular shape upon release of the stent and the bag from the catheter. In its preferred form, the stent comprises a resilient, flexible wire biased along a helical path conforming to the tubular shape to interfit within the tube forming the bag.

The invention also contemplates an assembly of the bag and the catheter ready to be used to treat the aneurysm. The assembly comprises a catheter having a lumen, the bag being in the second, smaller diameter shape and positioned within the lumen, the bag being slidable through the lumen for insertion into the saccular aneurysm.

The invention also includes a method of forming a flexible bag defining an enclosed space and adapted to fit within a catheter lumen and expand to substantially occupy a blood-filled saccular vascular aneurysm. The enclosed space is adapted to receive the blood and a clotting medium, for example, a length of wire, for promoting clotting. The preferred method of forming the bag comprises the steps of:

(a) braiding a plurality of flexible resilient filamentary members into a resiliently deformable tube of predetermined length and predetermined first diameter sized to substantially fill the aneurysm, the tube having open ends oppositely arranged;

(b) biasing the filamentary members into a first shape state substantially maintaining the tube in a radially expanded shape at the first diameter, the filamentary members being resiliently deformable into a second shape state wherein the tube is collapsed to a second diameter smaller than the first and sized to slidingly interfit within the catheter lumen;

(c) biasing the filamentary members radially inwardly at the ends to form constrictions substantially closing off the ends, the filamentary members being resiliently deformable radially outwardly of the tube providing an opening for access to the enclosed space within the bag for receiving the clotting medium therein.

Preferably, the braiding step is performed over a mandrel having a bulbous shape in order to help establish the biasing of the filamentary members into the expanded first diameter as well as the constrictions closing off the open ends of the tube. The biasing step is conveniently performed by applying heat to the filaments while the filaments are on the mandrel, thereby fixing the biased shape.

When it is desired to use supplemental filaments to augment the extension and/or support of the bag, further method steps are included such as:

(d) interbraiding a plurality of radiopaque monofilament wires with the filamentary members forming the tube; and (e) biasing the wires into the first shape state, the wires being resiliently deformable into the second shape state.

As previously mentioned, the radiopaque wires are resiliently collapsible to the second diameter to interfit within the catheter lumen. The wires push radially outwardly to support the bag when the bag expands to the first diameter upon release from the catheter.

When the embodiment according to the invention includes the catheter, the method also includes the step of positioning the bag within the lumen of the catheter, the bag being collapsed to the second, smaller diameter to slidingly interfit within the lumen.

It is an object of the invention to provide a bag useful in the treatment of vascular saccular aneurysms.

It is another object of the invention to provide a bag insertable into a vascular saccular aneurysm.

It is another object of the invention to provide a bag which can be used to contain a clotting medium, the bag serving to prevent undesired blood clots from forming in the vascular system but to promote blood clot formation in the aneurysm.

It is yet another object of the invention to provide a bag which is resiliently deformable between two shape states, one of which is expanded to substantially fill the saccular aneurysm, the other of which is collapsed to slidingly interfit within a catheter lumen for insertion into the aneurysm.

It is still another object of the invention to provide a bag resiliently biased to nominally assume the expanded shape state.

It is again another object of the invention to provide a means for augmenting the expansion and support of the bag in the expanded shape state.

It is yet again another object of the invention to provide a bag which holds a clotting medium comprising a wire used for electrothrombosis within a saccular vascular aneurysm.

It is still another object of the invention to provide a bag which is self expanding to said expanded shape state upon release from the catheter lumen.

These and other objects of the invention can be discerned from a consideration of the following drawings and detailed description of the invention.

BRIEF DESCRIPTION OF THE DRAWINGS

FIG. 11 shows a partial cross sectional view of still another alternate embodiment of the bag shown in FIG. 3; and FIG. 12 is a flow chart describing a method of manufacturing a bag according to the invention.

DETAILED DESCRIPTION OF A PREFERRED EMBODIMENT

The problem of a wire end protruding from an aneurysm into an artery in the treatment of saccular aneurysms can be eliminated by lining the aneurysm with a porous bag which will receive the wire and the blood in the aneurysm and contain the wire tangle wholly within the bag. Blood will still clot on the wire and form an occlusion sealing the aneurysm, but no part of the wire will extend out from the bag into the artery where clots can form to break away and cause complications.

Figure 1:
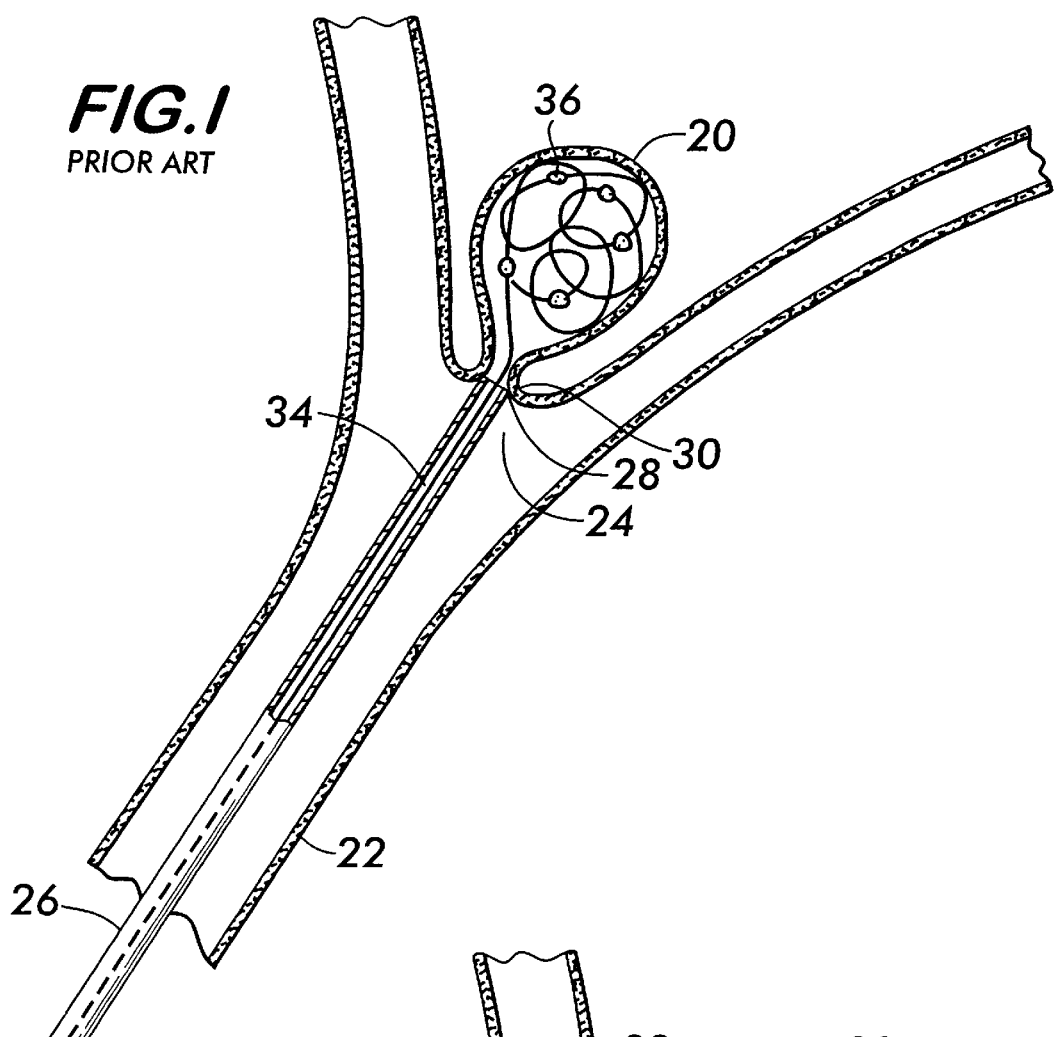
FIG. 1 shows a longitudinal sectional view of a saccular aneurysm in an artery being treated by a prior art intravascular catheter technique.
Figure 2:
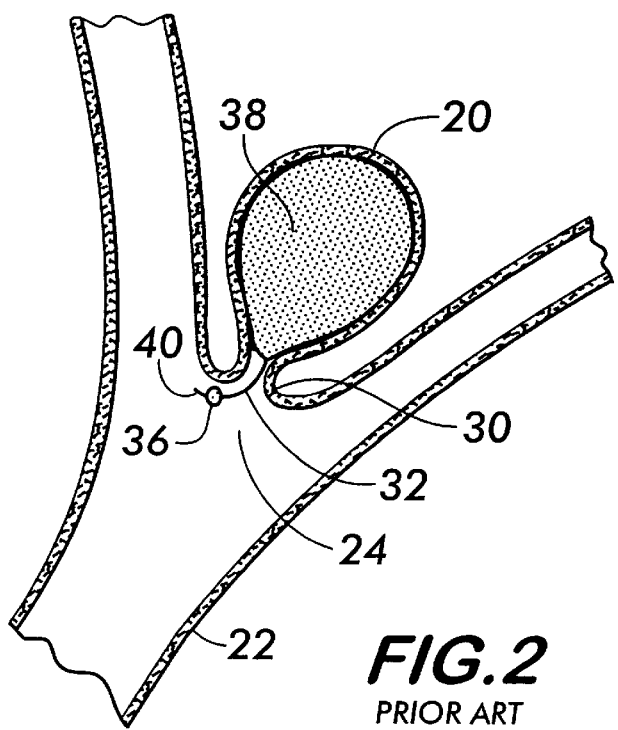
FIG. 2 shows a longitudinal sectional view of the saccular aneurysm in FIG. 1, but at a different stage in the treatment as compared with FIG. 1.
Figure 3:
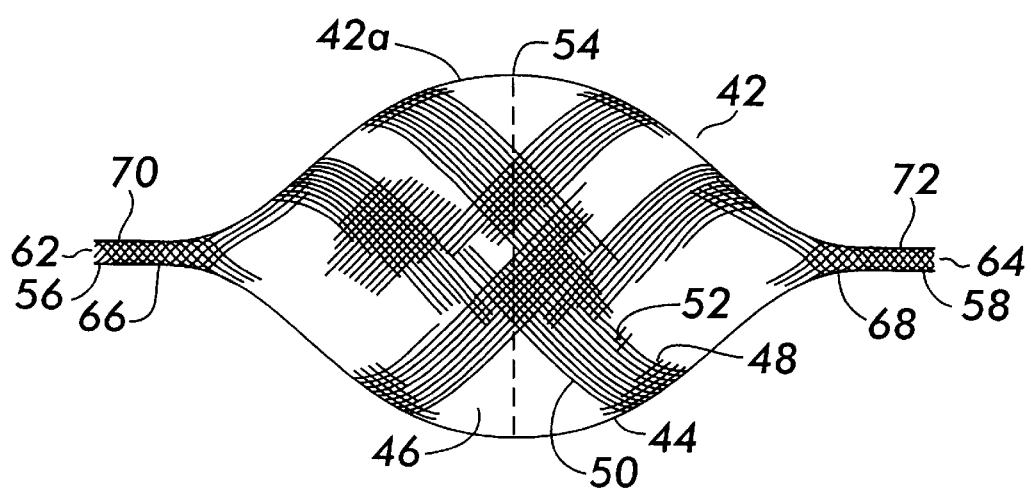
FIG. 3 shows a side view of a bag according to the invention, the bag being in a first shape state having an expanded diameter.

FIG. 3 shows a bag 42 suitable for use with the above described aneurysm treatment technique. Bag 42 preferably comprises a sleeve 44 defining an enclosed space 46, the sleeve being formed by a circular braid 48 of multifilament yarns 50. Monofilament yarns could also be used but multifilament yarns are preferred because they provide enhanced flexibility. Textured yarns, flat yarns, microdenier (less than 1 denier per filament), as well as yarns formed from slit tape or film, are also found feasible. Polyester is the preferred material for the yarns due to its inherent resilience, biological compatibility and long history of success in human implant use.

Yarns 50 preferably range from 5 to 100 denier and are interlaced in a relatively dense braid, the braid density and the denier being controlled to achieve a fine braid structure having a relatively high porosity (50%–80%) with relatively small interstices 52 forming pores which allow blood to flow into the enclosed space 46 of bag 42 relatively unimpeded, but prevent the wire end 40 from extending outwardly through the bag. The porosity is quantified by the ratio of the total area of the openings (interstices) in the bag to the total surface area of the bag, multiplied by 100. Preferably, the space between yarns should be no larger than half a yarn diameter.

Differing mesh densities can be effected by controlling the denier of the yarns and the number of carriers on the braiding machine in relation to the circumference of the sleeve. To create the range of mesh densities of yarns 50 preferred for the bag 42, between 36 and 144 carriers can be used to feed yarns having a denier between 5 and 100 to the braiding machine forming a sleeve having a circumference between 0.75 and 1.25 inches (0.6–1 cm in diameter). A preferred braiding set up features 72 filaments of 40 denier polyester yarn braided over a 6 mm mandrel at a braid angle of 37°. This configuration achieves a porosity of 80%. In an alternate embodiment, 132 filaments of 20 denier polyester yarn are braided over a 6 mm (0.23 inch) mandrel at a braid angle of 37°, achieving a porosity of 78%. The denier of the yarn and the mesh density also affect the relative flexibility of the bag with higher mesh densities yielding relatively stiffer bags.

Yarns 50 are preferably interlaced by braiding to take advantage of the well known "trellis effect" exhibited by braided textiles, i.e., the braided yarns comprising the bag rotate and slide relatively to one another when a force is applied to the bag. This effect results in radial contraction of the bag with axial expansion and radial expansion upon axial contraction.

Figure 4:
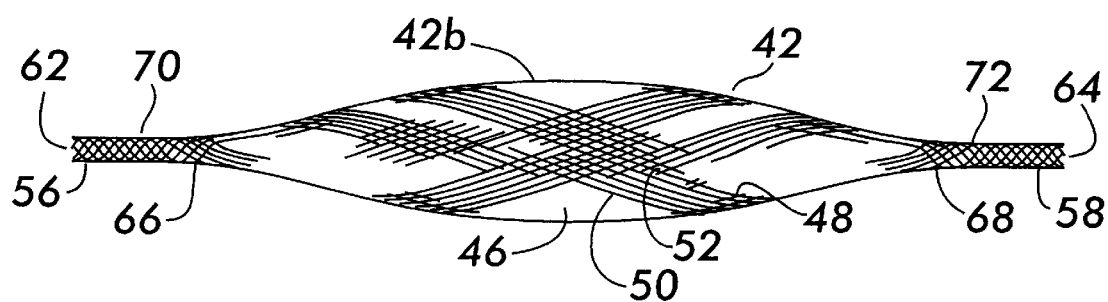
FIG. 4 shows a side view of the bag in FIG. 3, the bag being in a second shape state having a smaller diameter.

The resilience and flexibility of the yarns 50 coupled with the characteristics of the "trellis effect" realized by using the braided structure 48 allows bag 42 to be resiliently deformed and assume at least two distinct shape states illustrated in FIGS. 3 and 4. FIG. 3 depicts bag 42 in an expanded shape state denoted 42a, the bag having an expanded diameter 54 sized to substantially fill the aneurysm 20.

The other shape state, 42b, is illustrated in FIG. 4 and shows the bag 42 resiliently deformed into a thin, elongated cylinder which can easily pass through the lumen 34 of catheter 26.

The yarns 50 are resiliently biased so that bag 42 naturally assumes the expanded diameter shape state 42a, seen in FIG. 3, when not restrained by external forces. The other shape state, 42b, is assumed by the bag when it is stretched longitudinally between its ends 56 and 58, the yarns 50 of the braid structure 48 resiliently deforming and rotating relative to each other (the "trellis effect") to collapse the expanded diameter and convert bag 42 from its expanded shape state 42a to its smaller diameter, collapsed shape state 42b without kinking or wrinkling.

Figure 5:
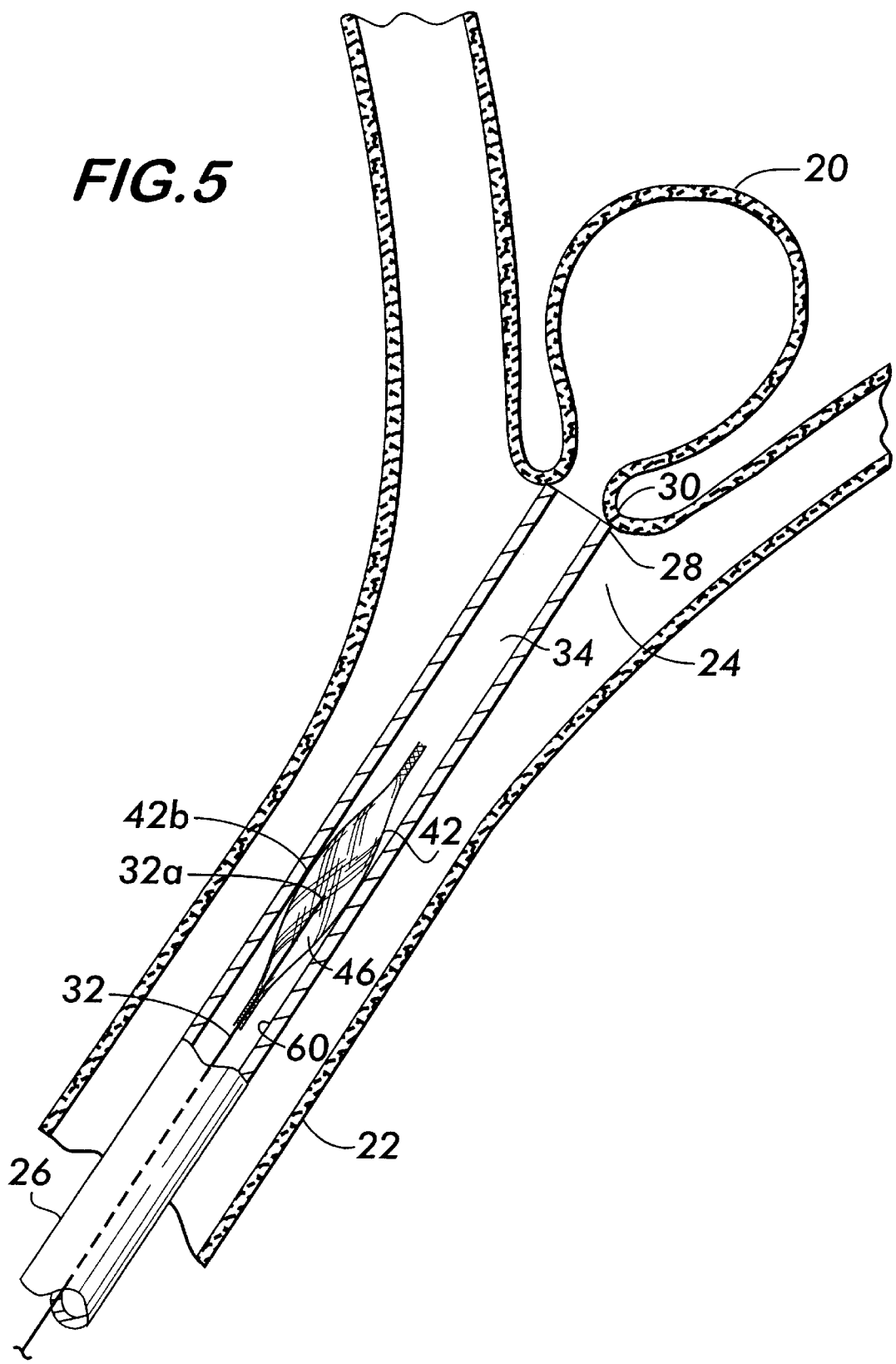
FIG. 5 shows a longitudinal sectional view of a saccular aneurysm in an artery being treated by an intravascular catheter technique using the bag shown in FIGS. 3 and 4.
Figure 6:
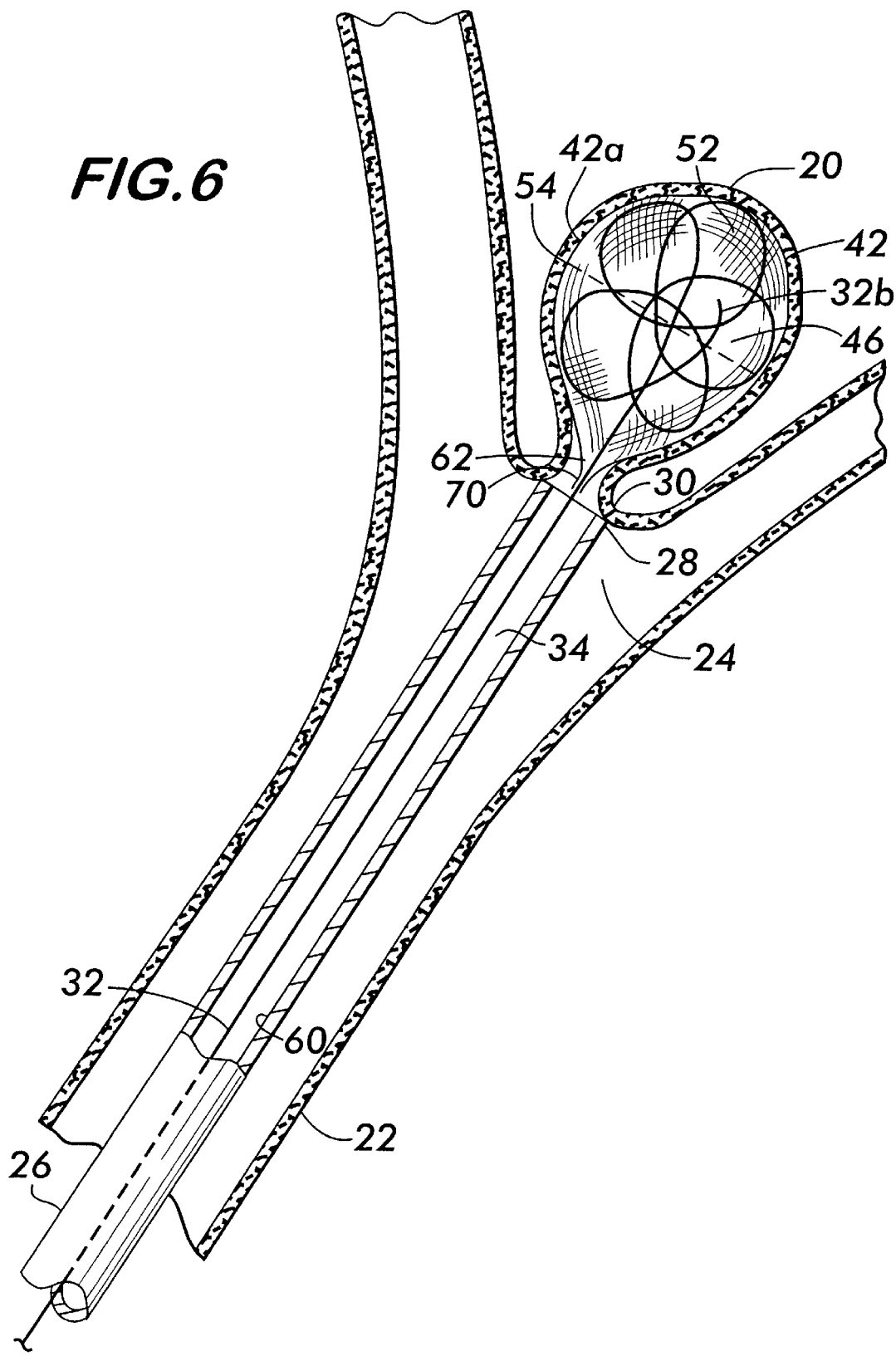
FIG. 6 shows a longitudinal sectional view of the saccular aneurysm seen in FIG. 5, but at a different stage in the treatment as compared with FIG. 5.

When under tension and forced into the collapsed shape state 42b, the bag 42 slidingly interfits within lumen 34 as illustrated in FIG. 5. The bag is held in that shape state by contact with the wall 60 of the catheter while positioned within the lumen. When the bag is forced out of the lumen, as seen in FIG. 6, it will expand to its larger diameter shape state 42a due to the biasing of the yarns 50.

Although the braided bags can be effectively produced over a wide range of dimensions, practical braided bags 42 for use in treating saccular aneurysms preferably have a length from end to end of about 0.4 inches (1 cm) and a maximum diameter of about 0.4 inches (1 cm) when in the first shape state 42a, and a length of about 0.59 inches (1.5–1.6 cm) and a substantially uniform diameter of 0.079 inches (2 mm) or less when stretched into the collapsed shape state 42b.

In its preferred embodiment, bag 42 has at least one opening through which it can receive platinum wire 32 once the bag is positioned in aneurysm 20 and expanded into its larger diameter shape state 42a. When the bag is formed from a braided sleeve, such as 44, there are generally two openings, 62 and 64, located at either end 56 or 58 respectively, of the sleeve. If closures are not provided for these openings, wire end 40 will not necessarily be contained within bag 42 (or aneurysm 20) and the wire end may extend outwardly through one of the openings into the artery 22 despite the presence of bag 42.

It is preferred to provide closures 66 and 68 for openings 62 and 64 by biasing yarns 50 radially inwardly of sleeve 44 at each end 56 and 58 to form constrictions 70 and 72 in the bag. Yarns 50 are biased to lie contiguous with each other forming constrictions 70 and 72 which pinch off the openings 62 and 64. The yarns can be resiliently deformed away from the openings, however, to expand the constrictions and allow access to the enclosed space 46 within the bag 42 through the openings 62 and 64. This allows the wire, or other medium for promoting clotting, to be inserted into the bag. Due to the biasing of the yarns 50, the yarns around the opening 62 naturally assume the constricted shape, thus, closing off the openings when the bag 42 is unstressed by external forces, as when it is within aneurysm 20.

If it is desired to augment the biasing forces which expand and support the bag 42 in its expanded diameter shape state 42a, supplemental filaments can be incorporated into the bag. The supplemental filaments are best formed from material having greater resiliency than the yarns 50 comprising the bag. Shape-memory metals, such as nitinol, are particularly useful as supplemental filaments because they provide increased biasing forces tending to expand and support the bag in the expanded large diameter shape state. Nitinol is also radiopaque and thus provides a means for viewing the bag by fluoroscopy or X-ray techniques. Other materials suitable for use as supplemental filaments include stainless steel and elgiloy. Practical diameters for the supplemental filaments range from 0.005 to 0.009 inches.

Figure 8:
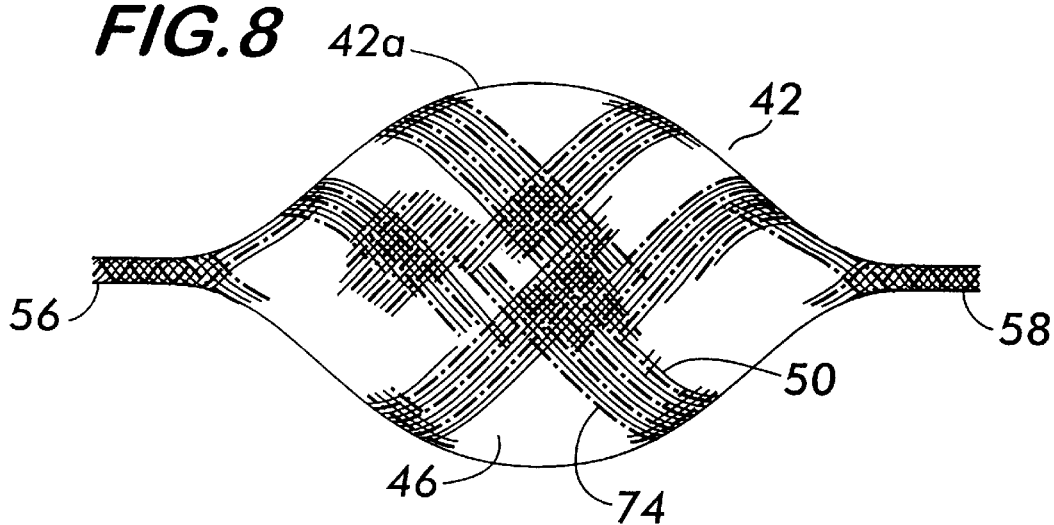
FIG. 8 shows a side view of one alternate embodiment of the bag shown in FIG. 3.
Figure 9:
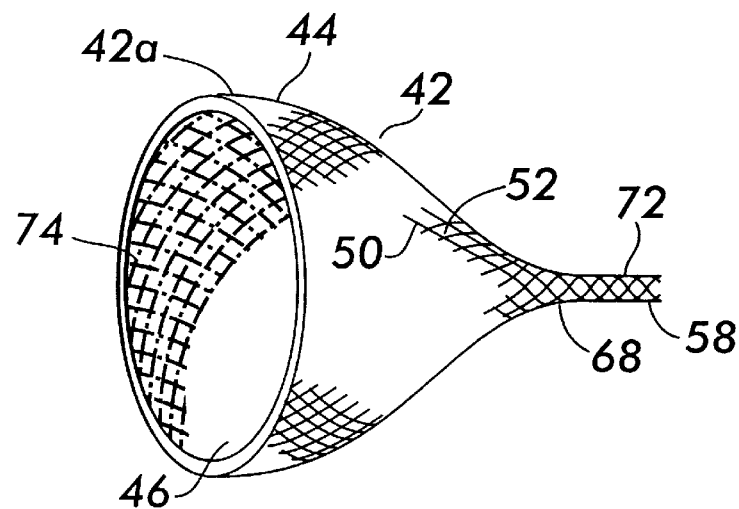
FIG. 9 shows a partial perspective view of another alternate embodiment of the bag shown in FIG. 3.
Figure 10:
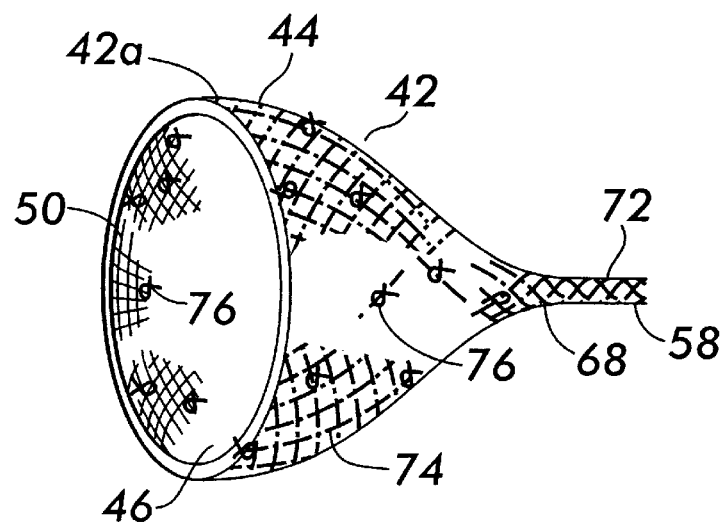
FIG. 10 shows a partial perspective view of yet another alternate embodiment of the bag shown in FIG. 3.

As seen in FIG. 8, supplemental filaments 74 (shown in broken line for clarity of illustration) are interbraided with yarns 50. While interbraiding the supplemental filaments with the yarns is preferred, the supplemental filaments 74 could also be arranged interiorly of bag 42 (see FIG. 9) or exteriorly (FIG. 10). Interiorly arranged supplemental filaments will push outwardly against the bag to expand and support it, while exteriorly arranged supplemental filaments would need to be attached to the bag, for example, by sutures 76, to exert direct support on the bag 42.

Expansion and support augmentation can also be provided by the use of a stent 78, as seen in FIG. 11. There are many forms of stents known for use in repairing vascular aneurysms, and they generally comprise a continuous, flexible, resilient support made from a metal alloy having relatively great resilience, a high yield stress and biocompatibility. The stent is preferably positioned within the bag and biased into a shape conforming to the expanded shape of the bag 42. The stent can be resiliently deformed into the collapsed shape state for slidingly interfitting within the catheter lumen 34. Upon release of the bag from the lumen, the stent expands due to its biasing and helps to expand and support the bag 42 in its expanded diameter shape state.

FIG. 12 shows a flow chart which describes a preferred method for forming a flexible bag according to the invention. The method includes the steps of braiding a plurality of flexible resilient filamentary members, such as yarns 50, into a resiliently deformable tube having a predetermined length and a predetermined first diameter sized to substantially fill the aneurysm 20. The yarns are then biased into a first shape state substantially maintaining the tube in a radially expanded shape at the first diameter. The yarns are, however, resiliently deformable into a second shape state, wherein the tube is collapsed to a second diameter, smaller than the first and sized to slidingly interfit with the catheter lumen. The next step forms the closures at each end of the bag by biasing the yarns radially inwardly to form the constrictions.

To aid in establishing the desired shape of the bag in its expanded shape state, the braiding step can be performed over a mandrel. Biasing of the yarns 50 is preferably accomplished by applying heat to the yarns while they are on the mandrel to set the yarns in the biased shape. Heat treatment parameters of temperature and time at temperature depend largely upon the particular yarn material but typically range between 100° C. to 200° C. for 10–15 minutes for yarns of practical interest. For example, polyester yarns have been successfully biased by heat treating for 15 minutes at 180° C. Other biasing methods, for example, by chemical means, are also feasible.

If expansion and support augmentation are desired, then the step of interbraiding resilient, bio-compatible wires with the yarns is included. It is advantageous to form the wires from radiopaque material, allowing the bag to be viewed by fluoroscopy or X-ray techniques. Finally, it may be desired to include the step of prepositioning the bag in its collapsed shape within a catheter for use in the treatment of a saccular aneurysm described below.

Description of a Method of Treating a Saccular Aneurysm

Figure 7:
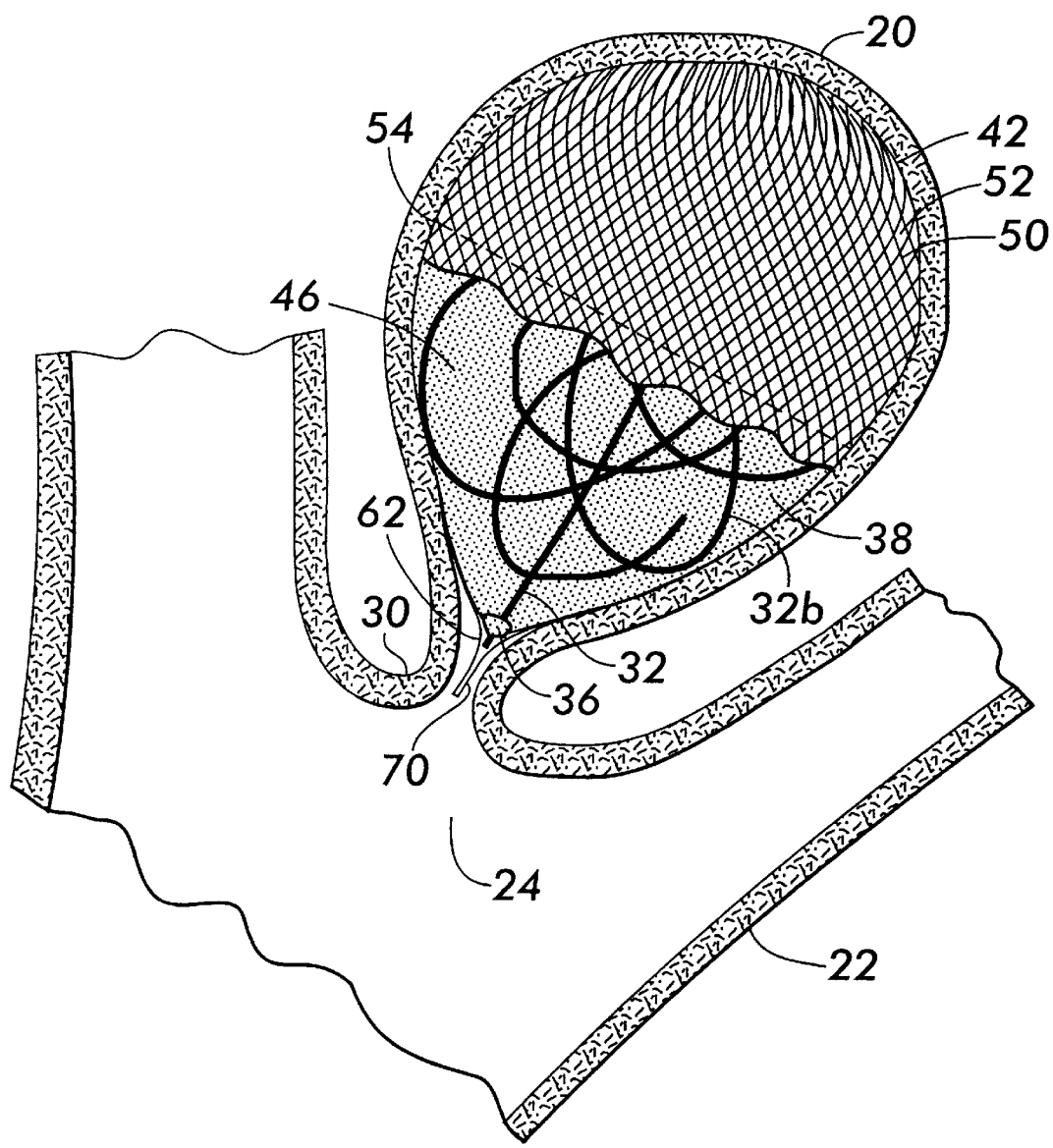
FIG. 7 shows the aneurysm depicted in FIGS. 5 and 6 on an enlarged scale.

FIGS. 5–7 illustrate a preferred method of treating a saccular aneurysm 20 using a braided bag 42 according to the invention by first positioning a catheter 26 containing bag 42 within its lumen 34 with the catheter tip 28 engaging the neck 30 of aneurysm 20 at the artery bifurcation 24. Bag 42 is in its second shape state 42b and thus is easily able to pass through lumen 34. Contact between the catheter wall 60 and the bag maintains it in the collapsed shape state. In the next step, seen in FIG. 6, bag 42 is forced out of the lumen and into the aneurysm 20, whereupon the bag expands as it leaves the catheter due to the biasing of yarns 50, the bag assuming the first shape state 42a having the constrictions 70 and 72 and the expanded diameter 54. Blood in the aneurysm enters enclosed space 46 through the pores formed by interstices 52.

Platinum wire 32, a tip portion 32a being prepositioned within the enclosed space 46 (see FIG. 5) is then snaked up through the catheter where it enters bag 42 through opening 62. A length of the wire is forced into the enclosed space 46 (now expanded to the large diameter 54) to form randomly tangled wire loops 32b. Blood in the bag clots on the wire. The clotting can be promoted by the process of electrothrombosis, as described above. After a relatively brief period, the clots form an occlusion 38 sealing off the aneurysm (see FIG. 7). At this point the wire 32 is released at end 36, the bag is disengaged from the catheter and the catheter is withdrawn from the artery. The constriction 70 closes off opening 62 due to the biasing of yarns 50 forming the constriction, and the entire wire 32 is contained within the bag within the aneurysm, including the end 36, which cannot extend out into the artery 22 and be a site for undesired clot formation.

The braided bag according to the invention, when used to contain a tangle of platinum wire or other clotting medium within a saccular aneurysm, should prevent an end of the wire from protruding outwardly from the aneurysm and into the artery. Thus, the wire will promote clotting within the aneurysm to form an occlusion but will not form a site in the artery where undesired clots can form, break away and cause an embolism. Use of the bag according to the invention in the treatment of vascular saccular aneurysms should reduce complications otherwise associated with this technique and measurably improve its success rate.

What is claimed is:

1. A flexible bag adapted to pass through a catheter lumen and expand to substantially occupy a fluid-filled cavity larger than said lumen, said bag being adapted to receive fluid within said cavity and a clotting medium for contact with said fluid, said bag comprising:

a plurality of interlaced flexible filamentary members;

a multiplicity of pores formed by interstices between said filamentary members, said pores being sized to allow said fluid to enter said bag but preventing outward extension of said clotting medium, said filamentary members being resiliently biased to assume an expanded first diameter substantially filling said cavity upon release from said catheter lumen, said filamentary members being resiliently deformable to a second diameter smaller than said first diameter and sized to slidingly interfit within said catheter lumen.

2. A flexible bag according to claim 1, wherein said clotting medium comprises a length of wire.

3. A flexible bag according to claim 2, wherein said length of wire is electrically conductive.

4. A flexible bag according to claim 2, further comprising an opening for receiving said length of wire into said bag, said filamentary members adjacent to said opening being resiliently biased to form a constriction in said bag closing off said opening and preventing an end of said length of wire from extending outwardly therethrough, said filamentary members being resiliently deformable away from said opening to expand said constriction and allow access to said bag through said opening.

5. A flexible bag according to claim 4, wherein said filamentary members are interlaced by braiding.

6. A flexible bag according to claim 5, wherein said filamentary members are multifilament polymer yarns.

7. A flexible bag according to claim 6, wherein said yarns are polyester.

8. A flexible bag according to claim 5, wherein said bag comprises an elongated tube, said opening being formed at an end of said elongated tube, said filamentary members adjacent to said open end being biased radially inwardly to form said constriction closing off said opening.

9. A flexible bag according to claim 8, further comprising a continuous flexible stent disposed within said bag, said stent being resiliently biased to conform to a tubular shape having a diameter substantially equal to said first diameter, said stent pushing radially outwardly to support said bag when expanded to said first diameter, said stent being resiliently deformable into a collapsed shape sized to slidingly interfit within said catheter lumen, biasing forces within said stent expanding said stent to said tubular shape upon release of said stent and said bag from said catheter lumen.

10. A flexible bag according to claim 9, wherein said stent comprises a resilient, flexible wire biased along a helical path conforming to said tubular shape.

11. A flexible bag according to claim 8, further comprising a plurality of supplemental, resilient filaments contiguous with said filamentary members, said supplemental filaments being biased to conform to a tubular shape having a diameter substantially equal to said first diameter, said supplemental filaments pushing radially outwardly to augment the support of said bag when expanded to said first diameter, said supplemental, resilient filaments being deformable into a collapsed shape sized to slidingly interfit within said catheter lumen, biasing forces within said filaments expanding said bag to said tubular shape upon release of said bag from said catheter lumen.

12. A flexible bag according to claims 11, wherein said supplemental filaments are interbraided with said filamentary members.

13. A flexible bag according to claim 11, wherein said supplemental filaments are positioned interiorly of said bag.

14. A flexible bag according to claim 11, wherein said supplemental filaments are radiopaque monofilament wires.

15. A flexible bag according to claim 14, wherein said supplemental filaments are made of nitinol.

16. A flexible bag defining an enclosed space, said bag being adapted to pass through a catheter lumen for insertion into a blood-filled saccular vascular aneurysm, said bag being porous to allow for the passage of blood within the aneurysm and containing a length of wire in contact with said blood for promoting clotting, clotted blood substantially filling said enclosed space and sealing off said aneurysm, said bag comprising:

a plurality of interlaced flexible filamentary members surrounding said enclosed space, said filamentary members being resiliently biased to assume a first shape state wherein said bag is expanded to a first diameter sized to substantially fill said aneurysm, said filamentary members being resiliently deformable to a second shape state wherein said bag is collapsed to a second diameter smaller than said first diameter and sized to slidingly interfit within said catheter lumen, said resilient biasing of said filamentary members expanding said bag to said first diameter upon release from said catheter lumen into said aneurysm;

an opening in said bag for receiving said length of wire into said enclosed space, said filamentary members having end portions biased to form a constriction in said bag closing off said opening and preventing said wire from extending outwardly therefrom, said end portions being resiliently deformable away from said opening to expand said constriction and allow access to said enclosed space through said opening.

17. A flexible bag according to claim 16, wherein said filamentary members are interlaced by braiding.

18. A flexible bag according to claim 16, having a porosity between about 50% and 80%.

19. A flexible bag according to claim 18, wherein said filamentary members comprise monofilament yarns having a denier between about 5 and 100.

20. A flexible bag according to claim 19, wherein said filamentary members are made of polyester.

21. A flexible bag according to claim 16 further comprising a catheter having a lumen, said bag being in said second shape state and positioned within said lumen, said bag being slidable through said lumen for insertion into said saccular aneurysm.

22. A method of forming a flexible bag defining an enclosed space and adapted to fit within a catheter lumen and expand to substantially occupy a blood-filled saccular vascular aneurysm, said enclosed space adapted to receive said blood and a clotting medium for promoting clotting, said method comprising the steps of:

braiding a plurality of flexible resilient filamentary members into a resiliently deformable tube of predetermined length and predetermined first diameter sized to substantially fill said aneurysm, said tube having open ends oppositely arranged;

biasing said filamentary members into a first shape state substantially maintaining said tube in a radially expanded shape at said first diameter, said filamentary members being resiliently deformable into a second shape state wherein said tube is collapsed to a second diameter smaller than said first and sized to slidingly interfit within said catheter lumen;

biasing said filamentary members radially inwardly at said ends to form constrictions substantially closing off said ends, said filamentary members being resiliently deformable radially outwardly of said tube providing an opening for access to said enclosed space for receiving said clotting medium therein.

23. A method of forming a flexible bag according to claim 22, wherein said braiding step is performed over a mandrel having a bulbous shape.

24. A method of forming a flexible bag according to claim 23, wherein said biasing steps are performed by applying heat to said filaments while said filaments are on said mandrel.

25. A method of forming a flexible bag according to claim 22, further comprising the steps of:

interbraiding a plurality of radiopaque monofilament wires with said filamentary members forming said tube;

biasing said wires into said first shape state, said wires being resiliently deformable into said second shape state;

said wires being resiliently collapsible to said second diameter and interfitting within said catheter lumen, said wires pushing radially outwardly to support said bag when expanded to said first diameter upon release from said catheter.

26. A method of forming a flexible bag according to claim 22, further comprising the step of positioning said bag within the lumen of a catheter, said bag being collapsed to said second diameter to slidingly interfit within said lumen.

* * * * *